United States Patent
Lucas et al.

Patent Number: 5,475,174
Date of Patent: Dec. 12, 1995

[54] PROCESS FOR THE SELECTIVE HYDROGENATION OF COMPOUNDS COMPRISING ENDO AND EXOCYCLIC UNSATURATIONS

[75] Inventors: Christine Lucas, Jonage; Jean-Pierre Candy, Caluire; Jean-Marie Basset, Villeurbanne; Blaise Didillon, Rueil Malmaison; Jean-Paul Boitiaux, Poissy, all of France

[73] Assignee: Institut Francais du Petrole, Rueil Malmaison, France

[21] Appl. No.: 156,777

[22] Filed: Nov. 24, 1993

[30] Foreign Application Priority Data

Nov. 26, 1992 [FR] France ................... 92 14353

[51] Int. Cl.$^6$ ................... C07C 5/05
[52] U.S. Cl. ................... 585/273; 585/271
[58] Field of Search ................... 585/271, 273

[56] References Cited

U.S. PATENT DOCUMENTS

| | | | |
|---|---|---|---|
| 3,773,654 | 11/1973 | Rausch | 208/57 |
| 4,079,092 | 3/1978 | Hayes et al. | 585/268 |
| 4,152,365 | 5/1979 | Drehman | 585/256 |

FOREIGN PATENT DOCUMENTS 106343  6/1974  German Dem. Rep. .

OTHER PUBLICATIONS

Chemical Abstracts, vol. 82, No. 3, 20 Jan. 1975, Abstract No. 16404p.

*Primary Examiner*—P. Achutamurthy
*Attorney, Agent, or Firm*—Millen, White, Zelano, & Branigan

[57] ABSTRACT

The invention concerns a process for the selective hydrogenation of polyunsaturated cyclic compounds comprising at least one endocyclic carbon-carbon double bond and at least one terminal exocyclic carbon-carbon double bond, said double bonds not being conjugated, to form a mixture essentially containing the saturated ring compound and comprising at least one terminal exocyclic double bond, the process being carried out in the presence of hydrogen under a pressure of from 1 to 10 MPa and at a temperature of from 0° to 200° C., and in the presence of a catalyst including a support and (a) from 0.1 to 5% by weight of at least one metal from group VIII (iridium, osmium, nickel, palladium, platinum and rhodium) and (b) from 0.01 to 15% by weight of at least one metal from group IVa (tin, germanium and lead), the molar ratio between metals of group VIII and group IVa being between 0.3 and 3. The process is used for the hydrogenation of 4-vinylcylcohexene to vinylcyclohexane.

15 Claims, No Drawings

PROCESS FOR THE SELECTIVE HYDROGENATION OF COMPOUNDS COMPRISING ENDO AND EXOCYCLIC UNSATURATIONS

The invention concerns a process for the hydrogenation of a polyunsaturated cyclic compound comprising at least one endocyclic carbon-carbon double bond (that is to say in the ring) and at least one terminal exocyclic (outside the ring) carbon-carbon double bond, hydrogenation being effected selectively on the endocyclic double bond or bonds.

The process necessitates the use of a catalyst based on a metal of group VIII and an additional metal belonging to group IVa, being the family of tin (germanium, tin and lead).

The invention is particularly well suited to the catalytic hydrogenation of 4-vinylcyclohexene to give vinylcyclohexane.

4-Vinylcyclohexene (I) is a compound containing two carbon-carbon double bonds, one being endocyclic and the other exocyclic.

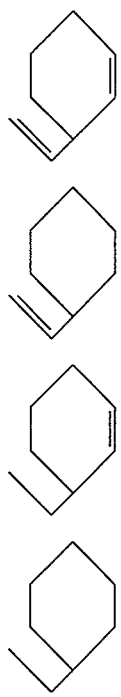

Catalytic hydrogenation of 4-vinylcyclohexene (I) can lead firstly to vinylcyclohexane (II) or ethyl-cyclohexene (III). Those two products can then be hydrogenated to give ethyl-cyclohexane (IV).

The catalytic reduction of 4-vinylcyclohexene (I) has been the subject of a certain number of works, either on heterogenous catalysts (U.S. Pat. No 4,716,256 for example) or on homogenous catalysts. However in most of the cases reported in the literature, the two majority products obtained are ethyl-cyclohexene (III) and ethyl-cyclohexane (IV).

In contrast, in U.S. Pat. No 3,154,594, vinylcyclohexane is prepared from 4-vinylcyclohexene by reacting the 4-vinylcyclohexene with an organoaluminium (for example triisobutyl aluminium), the compound obtained is hydrogenated in the presence of a catalyst selected from the group formed by palladium, platinum and Raney nickel. Vinylcyclohexane is isolated by heating the hydrogenated product at 100° to 200° C. in the presence of an olefin having a terminal unsaturation (for example dodec-1-ene).

It has been discovered in the present invention that it is possible to effect in a single step selective hydrogenation of 4-vinylcyclohexene (I) to give vinylcyclohexane (II) without obtaining ethyl-cyclohexene and while limiting the production of ethyl-cyclohexane (IV). Operation is effected in a continuous or discontinuous reactor in the presence of hydrogen under a total pressure of between 1 and 10 MPa and preferably between 1 and 5 MPa and at a temperature of between 0° and 100° C. and preferably between 20° and 50° C. in the presence of a catalyst comprising a support and (a) at least one metal from group VIII selected from the group formed by iridium, osmium, nickel, palladium, platinum and rhodium (rhodium being the preferred metal) and in respect of which the percentage by weight is selected at between 0.1 and 5% and preferably between 1 and 3%, and (b) at least one additional metal selected from group IVa formed by tin, germanium and lead, in respect of which the percentage by weight is selected at between 0.01% and 15%. The molar ratio of the element from group VIII to the element from group IVa is between 0.3 and 3 and preferably between 0.8 and 2.5. The support can be selected from refractory oxides and in particular the group formed by silica, alumina, silica-aluminas, as well as supports based on carbon and in particular charcoal and graphite.

The catalyst can be prepared by different procedures for impregnating the support. The impregnation operation for example involves bringing the support into contact with an aqueous or organic solution of a compound of the selected metal or metals. The metal or metals of group VIII and the additional metal or metals can be introduced simultaneously or in succession. After contact between the support and the solution has been maintained for several hours, the impregnated support is filtered, washed with water or with a hydrocarbon, dried and roasted in air at between 110° C. and 600° C. and preferably between 100° C. and 500° C.

Operation is preferably effected with two successive impregnation steps: the support is first subjected to an impregnation step by means of an aqueous or organic solution of at least one compound of metal from group VIII. The impregnated support is then filtered, dried, possibly washed with water or with an organic solvent, and roasted in air usually at between 110° C. and 600° C. and preferably between 110° C. and 500° C. and then reduced in hydrogen at a temperature of between 200° C. and 600° C. approximately and preferably between approximately 300° C. and 500° C.; the product obtained is then impregnated with an aqueous or organic solution of a compound of germanium, tin and/or lead. Advantageously, the procedure involves using a solution of at least one alkyl or aryl germanium, alkyl or aryl tin, alkyl or aryl lead, in accordance with the technology described in the present applicants' U.S. Pat. No. 4,548,918.

Among the organic solvents which can be used in accordance with the invention, mention may be made by way of example of hydrocarbons, halogenated hydrocarbons, ketones, ethers and aromatic derivatives. When the compound of germanium, tin or lead is liquid or gaseous under the impregnation conditions, the solvent is not indispensable.

After contact between the impregnated support of the metal or metals of group VIII and the solution containing at least one compound of group IVa selected from germanium, tin or lead has been maintained for a given period of time of between 0.2 and 10 hours at a temperature which is generally between 20° C. and 150° C., the product is possibly washed by means of the solvent used for impregnating the compound of group IVa, possibly dried and possibly roasted in air at a temperature of between 90° C. and 600° C. and reduced at between 50° and 600° C. or possibly used directly after impregnation of the compound or compounds of group IVa.

Another method involves working the moist support powder with the precursors of the catalyst and then shaping and drying same.

Examples of the metallic precursors which can be used in preparation of the catalyst are as follows: for metals from group VIII, it is possible to use compounds such as chlorides, nitrates, haloamino compounds, amino compounds and organic acid salts.

It is also possible to use organometallic compounds of a metal from group VIII in solution in an organic solvent, for example a hydrocarbon. As examples of hydrocarbons, mention may be made of saturated paraffinic hydrocarbons in which the chain contains from 6 to 12 carbon atoms per molecule or aromatic hydrocarbons containing an equivalent number of carbon. By way of examples of organometalic compounds of metal from group VIII, mention may be made of carbonyl and halocarbonyl compounds and acetylacetonates, without that list being limitative.

The elements selected from the group formed by tin, germanium and lead may be introduced in the form of polyketonic or hydrocarbyl complexes such as alkyls, aryls and alkyl aryls. The operation of introducing the metal or metals of group IVa is advantageously effected by means of a solution in an organic solvent of the organometallic complex of said metal. As an organometallic compound of the metal of group IVa, particular mention will be made of tetrabutyltin, tetramethyltin, tetraethyltin, tetrapropyltin, tetraethylgermanium, tetramethylgermanium, tetraethyllead, diphenyltin, tributyltin hydride and tributyltin chloride, without that list being exhaustive. The impregnation solvent is selected from the group formed by paraffinic, naphthenic and aromatic hydrocarbons containing from 6 to 12 carbon atoms per molecule and halogenated organic compounds containing from 1 to 12 carbon atoms per molecule. Mention may be made of n-heptane, methylcyclohexane, toluene and chloroform. It is also possible to use well defined mixtures of the foregoing solvents or other solvents.

The element selected from the group formed by tin, germanium or lead may also be introduced by way of compounds such as chlorides, bromides, nitrates and acetates of tin; oxides, oxalates and chlorides of germanium; and halides, nitrates and acetate of lead in aqueous or organic solution.

The support may be of varying nature, as already mentioned above. A particularly suitable support has specific characteristics such as a specific area as determined by the BET method of between 10 and 500 $m^2$ per green and a total porous volume of from 0.2 to 1.3 $cm^3$ per green of support.

Once the metals are fixed on the support the catalyst can possibly be subjected to an activation treatment in hydrogen at between 50° and 600° C. However that step is not always necessary.

The following non-limiting examples illustrate the invention.

EXAMPLE 1

Comparative Test

Preparation of the catalyst is effected by impregnation of rhodium chloropentamine chloride in ammoniacal solution on a silica whose specific surface area is equal to 200 $m^2$ per gram and whose total porous volume is equal to 0.8 $cm^3$ per gram, followed by filtration, washing with distilled water and roasting in air at 450° C.

The fixed catalyst contains 1.9% of rhodium and will be referred to as catalyst A.

Catalyst A (0.0075 g) is then mixed with 0.1425 g of silica to result in catalyst B. Catalyst B is then reduced in hydrogen at 450° C., charged in a flow of argon into a reactor of stoneware type containing an organic solvent (n-heptane). The reactor is then closed and purged of the argon contained therein. Under an excess of hydrogen, the procedure then involves injecting a solution of 4-vinylcyclohexene (I) corresponding to an intial concentration of 0.154 mol/l of 4-vinylcyclohexene (I). The hydrogen pressure is then increased to 5 MPa; the temperature is kept constant at 22° C. The variation in the composition of the reaction mixture is followed by gaseous phase chromatography.

The results obtained are set forth in Table 1.

TABLE 1

| Time in minutes | Conversion (%) | Selectivity in (%) | |
|---|---|---|---|
| | | (II) | (IV) |
| 0 | 0 | — | — |
| 5 | 85 | 5.5 | 87 |
| 10 | 100 | 0 | 98 |

It will be seen that catalyst B has a high level of activity. In contrast, the levels of selectivity in respect of 4-vinylcyclohexane (II) are low. Catalyst B results in a major reduction of the two unsaturations of the 4-vinylcyclohexene, with the formation of ethyl-cyclohexane(IV).

EXAMPLE 2

According to the Invention

A rhodium-tin catalyst C is prepared from catalyst A in accordance with the following procedure. Catalyst A is firstly reduced in hydrogen at 450° C. The operation of fixing the tin is effected in a gaseous phase: tetrabutyltin is injected directly onto catalyst A at ambient temperature under a pressure of 2 kPa of hydrogen, then the temperature is increased in a controlled fashion at a rate of 100° C./hour to 350° C. while maintaining a low hydrogen pressure. Catalyst C produced in that way contains 1.9% by weight of rhodium and 2% by weight of tin.

Catalyst C is tested in the hydrogenation of vinylcyclohexene under the conditions of Example 1 (catalyst B).

The results obtained are set forth in Table 2.

TABLE 2

| Time in minutes | Conversion (%) | Selectivity in (%) | |
|---|---|---|---|
| | | (II) | (IV) |
| 0 | 0 | — | — |
| 15 | 31 | 91 | 8 |
| 60 | 62 | 85 | 15 |
| 350 | 100 | 0 | 100 |

Although catalyst C is less active than catalyst B, it makes it possible to achieve levels of selectivity in respect of vinylcyclohexane ( II ) which are markedly improved since at conversion rates of lower than 60% the level of selectivity in respect of vinylcyclohexane (II) is better than 85%.

EXAMPLE 3

According to the Invention

A rhodium-tin catalyst D is prepared from catalyst A using the procedure already described in the literature (U.S. Pat. No 4,456,775). The tin is impregnated in the form of tetrabutyltin in solution in normal heptane. After having left the catalyst and the tetrabutyltin solution in contact for 1 hour at the reflux temperature of the n-heptane, the catalyst is washed with n-heptane and then dried in a nitrogen atmosphere. The catalyst D obtained in that way contains 1.9% by weight of rhodium and 2% by weight of tin.

Catalyst D (0.150 g) is then charged in a flow of argon into the reactor of stoneware type containing an organic solvent (n-heptane). The reactor is then closed and purged of the argon contained therein. The procedure then involves the injection in hydrogen of a solution of 4-vinylcyclohexene (I) corresponding to an initial concentration of 0.154 mol/l of 4-vinylcyclohexene (I).

Hydrogenation of the 4-vinylcyclohexene (I) is then carried out under the conditions of Example 1.

TABLE 3

| Time in minutes | Conversion (%) | Selectivity in (%) (II) | (IV) |
| --- | --- | --- | --- |
| 0 | 0 | — | — |
| 30 | 41 | 92 | 7 |
| 60 | 63 | 88 | 12 |
| 90 | 74 | 87 | 12 |
| 120 | 82 | 85 | 15 |
| 360 | 100 | 15 | 95 |

Catalyst D is of an activity comparable to catalyst C but it makes it possible to achieve slightly better yields of vinylcyclohexane.

EXAMPLE 4

According to the Invention

Catalyst C (0.150 g) prepared in Example 2 is charged into a reactor of stoneware type containing an organic solvent, normal heptane, with the precautions specified in Example 2. The reactor is then closed and purged of the argon contained therein. The procedure then involves the injection in hydrogen of a solution of 4-vinylcyclohexene (I) corresponding to an initial concentration of 0.154 mol/l of 4-vinylcyclohexene (I). The hydrogen pressure is then increased to 2 MPa; the temperature is kept constant at 22° C. The variation in the composition of the reaction medium is followed by gaseous phase chromatography.

The results obtained are set out in Table 4.

TABLE 4

| Time in minutes | Conversion (%) | Selectivity in (%) (II) | (IV) |
| --- | --- | --- | --- |
| 0 | 0 | — | — |
| 15 | 21 | 92 | 8 |
| 60 | 42 | 90 | 9 |
| 350 | 85 | 87 | 13 |

Under a lower hydrogen pressure (2 MPa), catalyst C is less active than under elevated pressure (5 MPa), but the reduction in pressure makes it possible to increase the yield of vinylcyclohexene, which can attain 74%.

One skilled in the art will select the operating conditions (pressure, temperature, amount of $H_2$, residence time and amount of catalyst) in accordance with the level of selectivity in respect of product (II) which is desired for a given level of conversion.

We claim:

1. A process for the selective hydrogenation in the presence of a catalyst of a polyunsaturated cyclic compound comprising at least one endocyclic carbon-carbon double bond and at least one terminal exocyclic carbon-carbon double bond, said double bonds not being within aromatic cyclic structures or conjugated to form a mixture essentially containing a compound whose ring is saturated and which comprises at least one terminal exocyclic double bond, in which process the polyunsaturated cyclic compound is brought into contact in the presence of hydrogen at from 1 to 10 MPa and at a temperature of from 0° to 100° C. with a catalyst including a support and
   a) from 0.1 to 5% by weight of at least one metal from Group VIII selected from the group consisting of iridium, osmium, nickel, palladium, platinum and rhodium, and
   b) from 0.01 to 15% by weight of at least one metal from Group IVa selected form the group consisting of tin, germanium and lead, the molar ratio between said metal or metals of Group VIII and that or those of Group IVa being between 0.3 and 3.

2. A process according to claim 1 wherein the polyunsaturated cyclic compound is a substituted cyclohexene.

3. A process according to claim 1 wherein the polyunsaturated compound is 4-vinylcyclohexene which is hydrogenated to give vinylcyclohexane.

4. A process according to claim 1, wherein the pressure is between 1 and 5 MPa.

5. A process according to claim 1, wherein the temperature is between 20° and 50° C.

6. A process according to claim 1, wherein the metal of group VIII is rhodium and the metal of group IVa is tin.

7. A process according to claim 1, wherein the catalyst contains from 1 to 3% of at least one metal of group VIII.

8. A process according to claim 1, wherein the molar ratio between the metal (metals) of group VIII and the metal (metals) of group IVa is between 0.8 and 2.5.

9. A process according to claim 4, wherein the support is selected from the group consisting of refractory oxides and carbon-base supports.

10. A process according to claim 3, wherein the pressure is between 1 and 5 MPa, the temperature is between 20° and 50° C., the metal of Group VIII is rhodium, the metal of Group IV is tin, and the molar ratio of rhodium to tin is 0.8:1 to 2.5:1.

11. A process according to claim 1, wherein the metal of group VIII is rhodium and the metal of group IVa is tin.

12. A process according to claim 1 wherein the support is selected from the group consisting of refractory oxides and carbon-base supports.

13. A process for the selective hydrogenation in the presence of a catalyst of a polyunsaturated cyclic compound comprising at least one endocyclic carbon-carbon double bond and at least one terminal exocyclic carbon-carbon double bond, said double bonds not being conjugated, to form a mixture essentially containing a compound whose ring is saturated and which comprises at least one terminal exocyclic double bond, in which process the polyunsaturated cyclic compound is brought into contact in the presence of hydrogen at from 1 to 10 MPa and at a temperature of from 0° to 100° C. with a catalyst including a support and a) from 0.1 to 5% by weight of at least one metal from Group VIII selected from the group consisting of iridium, osmium, nickel, palladium, platinum and rhodium, and b) from 0.01 to 15% by weight of at least one metal from Group IVa selected form the group consisting of tin, germanium and lead, the molar ratio between said metal or metals of Group VIII and that or those of Group IVa being between 0.3 and 3 wherein selective hydrogenation of endocyclic carbon-carbon double bonds over exocyclic carbon-carbon double bonds in the polyunsaturated compounds is greater than 85%.

14. The process according to claim 11, wherein the pressure is between 1 and 5 MPa, the temperature is between 20° and 50° C., the metal of Group VIII is rhodium, the metal of Group IV is tin, and the molar ratio of rhodium to tin is 0.8:1 to 2.5:1.

15. A process according to claim 11, wherein the polyunsaturated compound is vinylcyclohexene which is hydrogenated to give vinylcyclohexane with better than 85% selectivity.

* * * * *